United States Patent [19]

Uytterhoeven et al.

[11] Patent Number: 4,514,520

[45] Date of Patent: Apr. 30, 1985

[54] CATALYST AND METHOD OF ITS PREPARATION

[75] Inventors: Jan Uytterhoeven, Leuven; Pierre Jacobs, Gooik; Ludo Adriaensen, Deerlijk; Jan Geerts, Sint-Katelijne-Waver, all of Belgium

[73] Assignee: N.V. Bekaert S.A., Zwevegem, Belgium

[21] Appl. No.: 548,826

[22] Filed: Nov. 4, 1983

[30] Foreign Application Priority Data

Nov. 18, 1982 [NL] Netherlands .................. 8204478

[51] Int. Cl.$^3$ .................. B01J 23/72; B01J 23/74
[52] U.S. Cl. .................. 502/337; 502/338; 502/345; 502/527; 148/6.3; 148/6.31; 148/6.35
[58] Field of Search .............. 502/337, 338, 345, 527; 148/6.3, 6.31, 6.35

[56] References Cited

U.S. PATENT DOCUMENTS

| | | | |
|---|---|---|---|
| 1,936,564 | 11/1933 | Barker | 23/233 |
| 3,469,297 | 9/1969 | Webber et al. | 428/605 |
| 3,485,595 | 12/1969 | Kraft | 502/527 X |
| 3,769,240 | 10/1973 | Lewi et al. | 502/345 X |
| 3,772,214 | 11/1973 | Nakamoto et al. | 502/184 |
| 3,957,682 | 5/1976 | Dorawala et al. | 252/373 |

FOREIGN PATENT DOCUMENTS 2206125  7/1974  France .

*Primary Examiner*—W. J. Shine
*Attorney, Agent, or Firm*—Shlesinger Arkwright Garvey & Fado

[57] ABSTRACT

A catalyst comprising a metallic carrier having a catalytically active metal-containing surface layer, the catalytic metal being other than a noble metal, whereby the catalytically active surface layer is formed out of a homogeneous metallic carrier by oxidizing in an oxidizing gas such as air and subsequently reducing with hydrogen the surface of the metallic carrier at a temperature at which the active metal is substantially not sintered, characterized in that the carrier is a web or felt of fibers with a diameter between 4 and 100 microns.

16 Claims, 3 Drawing Figures

0.1 mm 25.0 k V
Fig. 1  Catalyst according to the invention after the oxydation- and reduction reactions.
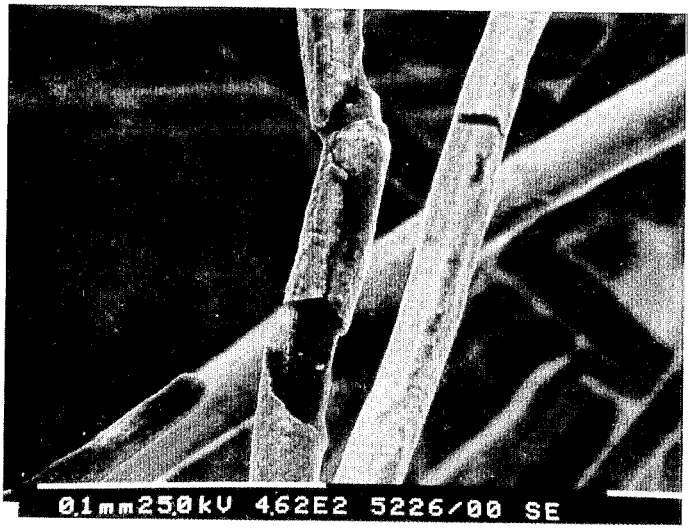
0.1 mm 25.0 k V
Fig. 2  Nickel fibers before the preparation of the catalyst. This picture shows the fibers of figure 1 after the oxydation but without reduction with a partially removed surface layer.

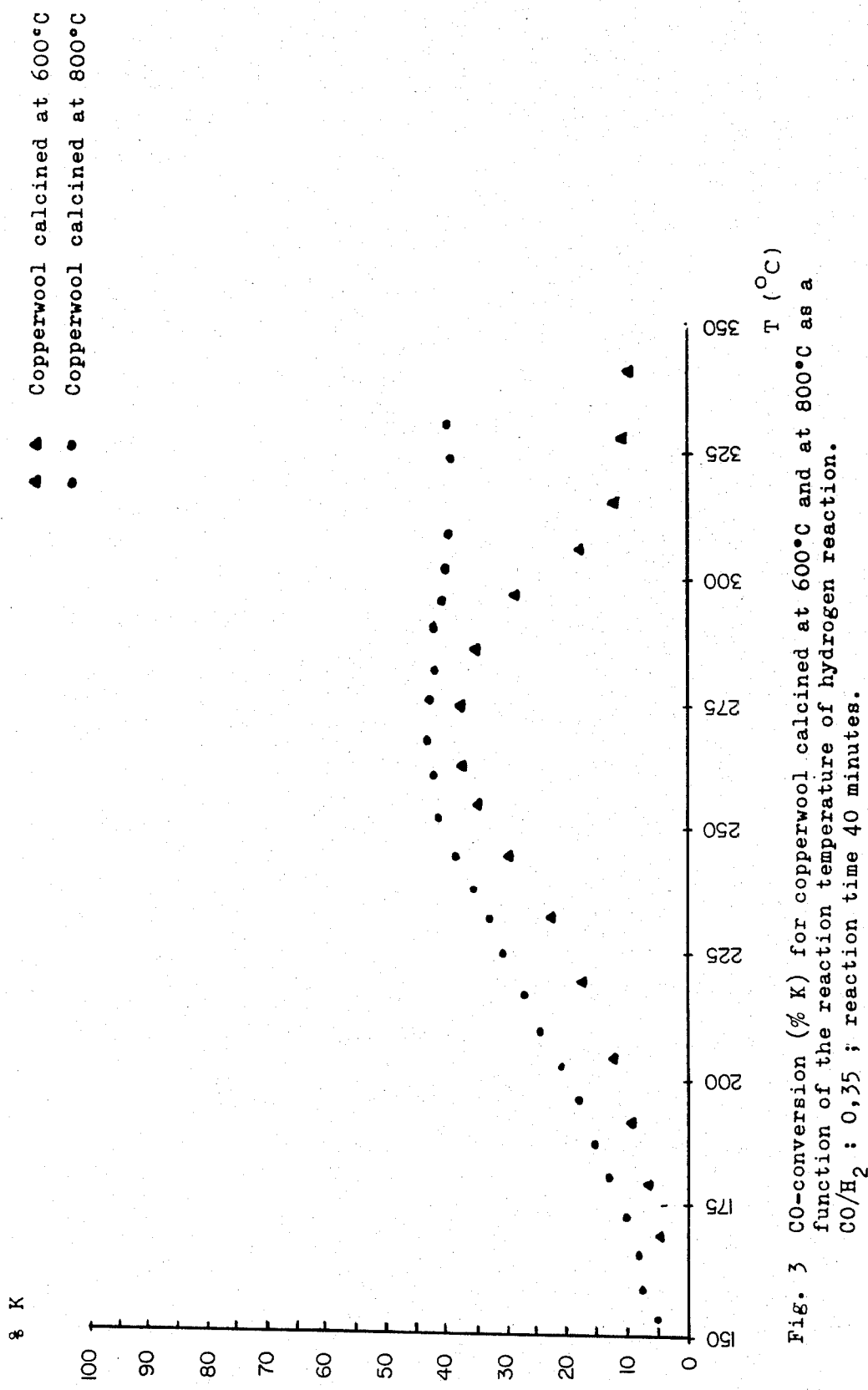
Fig. 3 CO-conversion (% K) for copperwool calcined at 600°C and at 800°C as a function of the reaction temperature of hydrogen reaction. CO/H$_2$ : 0,35 ; reaction time 40 minutes.

CATALYST AND METHOD OF ITS PREPARATION

The invention relates to a catalyst comprising a metallic carrier having a catalytic metal-containing surface layer with the exception of the noble metals, whereby the catalytic surface layer is formed of a homogeneous metallic carrier by oxidizing and subsequently reducing of the surface of the metallic carrier at a temperature at which the active metal is substantially not sintered together.

Such a catalyst, as well as a method for preparing such a catalyst is known from the U.S. Pat. No. 1,936,564.

However, the carrier or base according to the U.S. Pat. No. 1,936,564 consists of a cast object, whereby the proportion or ratio of the mass of the carrier with respect to the catalytic metallic surface layer is bad, the heat transfer of the massive carrier is not acceptable, and the catalyst cannot be used as filtration medium, through which catalytically-operated liquid media can only be obtained in a catalyst-free condition by means of separate filtration means.

The object of the invention is to provide a catalyst, which does not show the above-mentioned disadvantages.

According to the invention, the object is obtained, because the carrier is a web or felt of fibers with a diameter between 4 to 100 $\mu$m.

Such a catalyst according to the invention shows the big advantages, that it can easily be manufactured by subjecting the carrier exclusively to a surface treatment, that the metallic fibrous carrier can easily dissipate or drain away the heat generated during chemical reactions, that the metallic fibrous web shows a great mechanical strength and a low resistance against gas- or liquid flow so that the catalyst can easily be separated from a liquid medium after finishing the catalytic reactions, that the metallic fibrous web has a great surface and that the catalytically-operating spongy mass is held well protected within the web, through which the catalyst has a long term of life.

Moreover, the filtration capacity of the web can easily be regulated or changed by changing the thickness of the web.

A catalyst is already known, comprising a metallic screen or gauze covered with a catalytic metallic layer, obtained by depositing a solution of esters of an alcohol and an inorganic acid on the metal gauze wires, said inorganic acid containing a metal in the groups IVa to VIIa of the Periodic Table. From literature it is known to make use of e.g. a mixture of vanadic acid, permanganic acid and copper acetate esterified with cyclopentanol and ethylene glycol (see U.S. Pat. No. 3,951,866 and British Specification No. 1,440,789).

After applying this solution on the metal wires, the metallic gauze is dried, and after being heated up under the formation of a layer of active metal oxide it is finally reduced in a hydrogen atmosphere.

A similar catalyst is very useful in cleaning exhaust gases of diesel oil engines, but is less suitable for other chemical reactions than the web according to the invention.

BRIEF DESCRIPTION OF THE DRAWINGS

FIG. 1 shows a photographic enlargment of catalytically active nickel fibers prepared according to the present invention wherein the fibers have undergone oxidizing and reducing treatment.

FIG. 2 shows non-catalytically active nickel fibers which have undergone oxidation but not reduction.

FIG. 3 shows a graph plotting percentage of carbon monoxide conversion as a function of hydrogen reaction temperature for copperwool calcined at 600° C. and at 800° C.

Preferably, the catalyst according to the invention is formed by oxidizing and subsequently reducing of the surface of the metallic carrier at a temperature at which the active metal is substantially not sintered together and the carrier surface comprises at least one metal belonging to the group VIII and/or group Ib of the Periodic Table.

By oxidizing the surface of the fibers, such as nickel, nickel oxide is formed, which is subsequently reduced, e.g. by means of hydrogen.

The improved working of the catalyst according to the invention is probably due to the special manner of anchoring of the catalytically-active layer in the fibrous mass of the web or felt, since the catalytic layer is formed out of the original metallic carrier and should be kept anchored to the carrier as much as possible.

A catalyst according to the invention can also very easily be regenerated by reoxidizing and reducing.

It is a known method to prepare catalysts without a carrier by heating compounds of the abovementioned metals, generally nitrates, hydroxides, carbonates or basic carbonates, in the air under the formation of metal oxides which are subsequently reduced without sintering the catalytic metal parts. The preparation method has the drawback that the said metal compounds must be prepared first.

It is also possible to prepare such catalysts by reducing metal chlorides which, however, has the disadvantage that hydrogen-chloride-containing gases must be used next to the preparation of the metal chlorides.

The metal of the carrier surface of the catalyst according to the invention may consist of an alloy whereby it is of benefit that the alloy contains at least 50% active metal.

Preferably, the active metal is nickel, but also copper or iron are usable metals.

The carrier consists of fibers, which form a web or felt or metal woolmass. The fibers may also be bonded together by sintering their contacting surfaces.

The carrier effectively consists of a web or felt of fibers with a diameter ranging between 10 to 50 $\mu$m.

It must be noted that it is known to use noble metal gauzes, such as platinum gauzes, as well as strips of platinum-rhodium alloys, as catalysts for oxidizing ammonia into nitric acid (see German Application No. 1,594,716), whereas metal fiber webs are known as catalysts for catalytic afterburning of exhaust gases (see German Application No. 2,829,035).

It is further known to form a catalytic web or felt product on the basis of fibers made of silver, platinum, rhodium, palladium or alloy thereof. These catalysts, however, do not require a preliminary activating treatment, for example through oxidation and reduction, and are only used in reactions in the gas-phase with formation of gaseous endproducts, which have not to be filtrated.

Apart from a greater efficiency and its simple preparation, the catalyst according to the invention offers the great advantage that it can be very easily removed after the catalytic reaction. After the hydrogenization of fatty oils by means of a nickel catalyst, the latter must be filtered off, which for powder catalysts is a cumbersome treatment, whereas with the application of a catalyst according to the invention such a filtration step is not necessary at all since the catalyst, especially when in the form of a felt or web, may serve itself as a filtering medium.

It is a great advantage when the metal carrier is composed of nickel. Nevertheless, also other metals such as copper are good base products for forming a wire-shaped metallic carrier according to the invention.

In the case of nickel, the reduction occurs at a temperature below 500° C.

When the wire-shaped metallic carrier in the form of a web or felt is submitted to oxidation and reduction, care must be taken that during the reduction the temperature stays below the temperature at which the catalytic activity gets lost possibly through sintering the active spots. The fibers of the felt or web may obviously be bonded by sintering prior to the final reduction.

Evidently, the catalysts according to the invention may be supported by one or more grids.

The invention also relates to a method of forming a catalyst comprising a metallic carrier having a catalytic metal-containing surface layer, with the exception of the noble metals, whereby the catalytic surface layer is formed out of a homogeneous metallic carrier by oxidizing and subsequently reducing of the surface of the metallic carrier at a temperature, at which the active metal is substantially not sintered together, which method is characterized in, that the metallic carrier is fibershaped or formed out fibers with a diameter ranging between 4 to 100 $\mu$m, and that a web or felt is formed from such fibers either prior to or subsequent to the oxidizing and reducing treatments.

The catalyst is preferably formed by oxidizing and subsequently reducing the carrier surface at a temperature at which the active metal is not substantially sintered and the carrier surface comprises at least one metal belonging to the group VIII and/or group Ib of the Periodic Table.

Finally, the invention also relates to the application of a catalyst according to the invention in catalytic processes, particularly in the liquid phase, whereby the advantages are the fact that the catalysts according to the invention possess a very great heat conductivity, a greater mechanical strength, and a small resistance against gas or liquid flow, so that in the form of a felt or web, they are usable as filtration medium.

EXAMPLE I

A nickel felt or web according to U.S. Pat. No. 3,469,297 with fibers of 22 $\mu$m and a weight of 150 g/m2 is oxidized in the air at a temperature of 800° C. for two hours, after which the nickel fibers are submitted to a reduction with hydrogen at 400° C. for two hours.

The thus prepared catalyst was used in the formation of benzene out of cyclohexane at various temperatures, whereby the results are obtained as shown in Table A. As can be further noticed one obtains with the catalyst according to the invention at high temperatures almost only methane. At low temperatures, large amounts of benzene are obtained. When using a nickel web or felt with fibers of 12 and 50 $\mu$m; also very good results are obtained.

EXAMPLE II

Nickel fibers are used having a diameter of 50 $\mu$m and obtained by milling nickel. The nickel wool is oxidized in the air at 800° C. for two hours and reduced at 400° C. for two hours.

Dehydrogenizing cyclohexane into benzene at different temperatures offers the results as shown in Table B.

The same results can be obtained with fibers extracted from the melt according to the process as described in the European Pat. No. 0000926.

EXAMPLE III

Copper wool with a fiber diameter of 35 $\mu$m obtained by milling is oxidized by heating in the air at 800° C. for two hours, after which follows a reduction with hydrogen at 200° C. for two hours. Heating speed 2° C./m.

Subsequently, the catalyst is used in the conversion reaction of carbon monoxide with steam under the formation of carbon dioxide and hydrogen.

The results of tests conducted on copper wool oxidized at temperatures of 600° C. and of 800° C. show that when heating at 600° C. the conversion of carbon monoxide with water is worse than when heating to 800° C. (see FIG. 3).

EXAMPLE IV

A nickel felt is used as the one described in Example I with fibers of a diameter of 22 $\mu$m for the hydrogenization of aceton in the gaseous phase under the formation of 2-propanol. Subsidiary reactions take place at higher temperatures.

EXAMPLE V

A nickel felt is used according to Example I for the hydrogenolysis of octane whereby, apart from methane, mainly heptane and hexane are formed, but whereby at raising temperature the amounts of ethane to heptane increase which at still higher temperatures are broken down to lower hydrocarbons.

EXAMPLE VI

A soya bean oil to be hydrogenized, as well as a nickel felt or web with a fiber diameter of 22 $\mu$m according to Example I are introduced into a reactor.

Hydrogenization with hydrogen takes place at a pressure of 1 kg/cm2 and at a temperature of 180° C. up to an iodine number of 60.

After finishing the reaction one directly obtains from the reactor a liquid compound which solidifies when cooled down and does not contain metal parts. Indeed, the felt or web was active as a filtering medium. In the FIGS. 1 and 2 electron microscopic pictures are shown of nickel fibers with a catalytic layer on the outer sides of the nickel fibers as well as its precursor. FIG. 1 shows the fibers after oxidation and reduction, while FIG. 2 shows the fibers after oxidation but without reduction. As can be seen the surface layer formed after the reduction is much more ductile than after oxidation.

EXAMPLE VII

Carbon monoxide is allowed to react with hydrogen in the presence of a nickel felt according to Example I. One obtains methane in water whereby it appears that the nickel catalyst greatly accelerates the reaction.

EXAMPLE VIII

Benzene is hydrogenized with hydrogen in the presence of a nickel felt according to the Example I, but with fiber diameters of 4 resp. 8, 12 and 22 $\mu$m. An excellent production of cyclohexane is obtained in all cases.

TABLE A

Dehydrogenization of cyclohexane at different temperatures over a nickel felt with 22 $\mu$m fibers.

| Temp. (°C.) | Weight % alkanes | | | | | | Benzene |
|---|---|---|---|---|---|---|---|
| | $C_1$ | $C_2$ | $C_3$ | $C_4$ | $C_5$ | $C_6$ | |
| 282 | 62,5 | 0,5 | 1,4 | 1,8 | 2,8 | 1,3 | 28,5 |
| 299 | 40,2 | 1,0 | 2,5 | 3,5 | 4,2 | 1,0 | 45,8 |
| 312 | 44,5 | 1,7 | 3,4 | 4,2 | 3,2 | 0,7 | 38,3 |
| 326 | 51,5 | 3,2 | 5,0 | 5,2 | 2,9 | 0,7 | 28,5 |
| 342 | 65,4 | 4,7 | 5,8 | 4,5 | 2,5 | 0,7 | 14,9 |
| 358 | 94,8 | 3,7 | 1,2 | 0,2 | — | — | — |
| 371 | 99,6 | 0,4 | — | — | — | — | — |
| 383 | 100 | — | — | — | — | — | — |

TABLE B

Dehydrogenization of cyclohexane at different temperatures over a nickel felt with 50 $\mu$m fibers.

| Temp. (°C.) | Weight % alkane | | | | | | Benzene |
|---|---|---|---|---|---|---|---|
| | $C_1$ | $C_2$ | $C_3$ | $C_4$ | $C_5$ | $C_6$ | |
| 291 | 70,0 | 0,2 | 0,3 | 0,5 | 1,0 | 0,2 | 24,6 |
| 306 | 62,3 | 0,4 | 0,8 | 1,1 | 1,0 | 0,2 | 32,2 |
| 324 | 43,1 | 0,8 | 1,6 | 1,6 | 1,6 | 0,2 | 36,8 |
| 334 | 59,7 | 1,6 | 2,4 | 1,7 | 1,2 | 0,1 | 31,8 |
| 346 | 64,0 | 2,2 | 2,9 | 2,1 | 1,8 | — | 25,9 |
| 359 | 74,1 | 2,6 | 2,6 | 1,5 | 0,6 | — | 18,4 |
| 373 | 81,1 | 2,7 | 2,3 | 0,9 | 0,3 | — | 12,5 |
| 386 | 87,0 | 3,2 | 1,7 | 0,6 | 0,2 | — | 7,3 |
| 400 | 99,8 | 0,2 | — | — | — | — | — |

We claim:

1. A catalyst comprising a metallic carrier having a catalytically active metal-containing surface layer, the catalytic metal being other than a noble metal, whereby the catalytically active surface layer is formed out of a homogeneous metallic carrier by oxidizing in an oxidizing gas and subsequently reducing the surface of the metallic carrier at a temperature at which the active metal is substantially not sintered, whereby the thus prepared catalytically active surface layer is in the form of a catalytically active metal-containing spongy mass, characterized in that the carrier is a web or felt of fibers with a diameter between 4 and 100 microns.

2. A catalyst according to claim 1, characterized in that the carrier surface comprises at least one metal belonging to the group VIII and/or group Ib of the Periodic Table.

3. A catalyst according to claim 1, characterized in that the metallic carrier contains nickel.

4. A catalyst according to claim 1, characterized in that the metallic carrier contains copper or iron.

5. A catalyst according to claim 1, characterized in that the metal of the carrier consists of an alloy.

6. A catalyst according to claim 3, characterized in that in the case of nickel the temperature of the reduction is below 500° C.

7. A catalyst according to claim 1, characterized in that the carrier consists of a web or felt of fibers with a diameter of 10 to 50 $\mu$m and that the fibers are bonded together by sintering at their contacting surfaces.

8. A method for forming a catalyst comprising a metallic carrier having a catalytically active metal-containing surface layer, the catalytic metal being other than a noble metal, whereby the catalytically active surface layer is formed out of a homogeneous metallic carrier by oxidizing in an oxidizing gas and subsequently reducing the surface of the metallic carrier at a temperature at which the active metal is substantially not sintered, whereby the thus prepared catalytically active surface layer is in the form of a catalytically active metal-containing spongy mass, characterized in that the metallic carrier is fiber-shaped or formed out of fibers with a diameter ranging between 4 and 100 microns, and wherein a web or felt is formed from said fibers.

9. A method according to claim 8, characterized in that the carrier surface comprises at least a metal belonging to the group VIII or Ib of the Periodic Table.

10. A method according to claim 8, characterized in that the metallic carrier contains nickel.

11. A method according to claim 8, characterized in that the metallic carrier contains copper or iron.

12. A method according to claim 8, characterized in that the metal of the carrier contains an alloy.

13. A method according to claim 10, characterized in that in the case of nickel, the reduction takes place at a temperature below 500° C.

14. A method according to claim 8, characterized in that the carrier consists of a web or felt of fibers with a diameter of 10 to 50 $\mu$m and that the fibers are bonded together by sintering at their contacting surfaces.

15. A method for forming a catalyst as in claim 8 wherein said web or felt is formed from said fibers prior to the oxidizing and reducing treatments.

16. A method for forming a catalyst as in claim 8 and wherein said web or felt is formed from said fibers subsequent to the oxidizing and reducing treatments.

* * * * *